United States Patent [19]

Obenchain

[11] Patent Number: 5,195,541
[45] Date of Patent: Mar. 23, 1993

[54] METHOD OF PERFORMING LAPAROSCOPIC LUMBAR DISCECTOMY

[76] Inventor: Theodore G. Obenchain, 12002 Royal Birkdale Row, #A, San Diego, Calif. 92128

[21] Appl. No.: 780,865

[22] Filed: Oct. 18, 1991

[51] Int. Cl.$^5$ ............................................. A61B 19/00
[52] U.S. Cl. ...................................... 128/898; 606/15; 606/46
[58] Field of Search ................. 606/13, 15, 45, 46; 128/898

[56] References Cited

U.S. PATENT DOCUMENTS

| | | | |
|---|---|---|---|
| 4,122,853 | 10/1978 | Smith | 606/11 X |
| 4,545,374 | 10/1985 | Jacobson | 606/61 |
| 4,573,448 | 3/1986 | Kambin . | |
| 4,583,539 | 4/1986 | Karlin et al. | 606/4 |
| 4,984,563 | 1/1991 | Renaud | 128/6 |
| 5,027,792 | 7/1991 | Meyer | 606/46 X |
| 5,084,043 | 1/1992 | Hertzmann | 606/13 X |
| 5,085,658 | 2/1992 | Meyer | 606/46 |

OTHER PUBLICATIONS

Burton, "Surgical Diskectomy 1991: Status Report", Seminars in Orthopedics, vol. 16, No. 2, Jun. 1991, pp. 92-97.
Karl Storz, Optical Forceps, BRO 4.
Karl Storz, Operating Laparoscope, LAP 3.

Primary Examiner—Stephen C. Pellegrino
Assistant Examiner—Jeffrey A. Schmidt
Attorney, Agent, or Firm—Jerry R. Seiler

[57] ABSTRACT

A discectomy apparatus comprises an elongated sleeve member having receiving means therein for an endoscope, receiving means for securing and suction and irrigation channel means, all secured and extending along the interior length of the sleeve. The apparatus is especially suitable for performing a laparoscopic lumbar discectomy. In another embodiment, an elongated sleeve member is provided with means for receiving an endoscope and means for removably receiving selected elongated surgical instruments.

The invention also includes an improved method for performing laparoscopic lumbar discectomy.

4 Claims, 3 Drawing Sheets

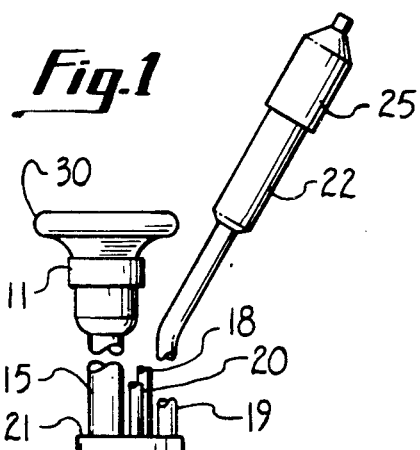
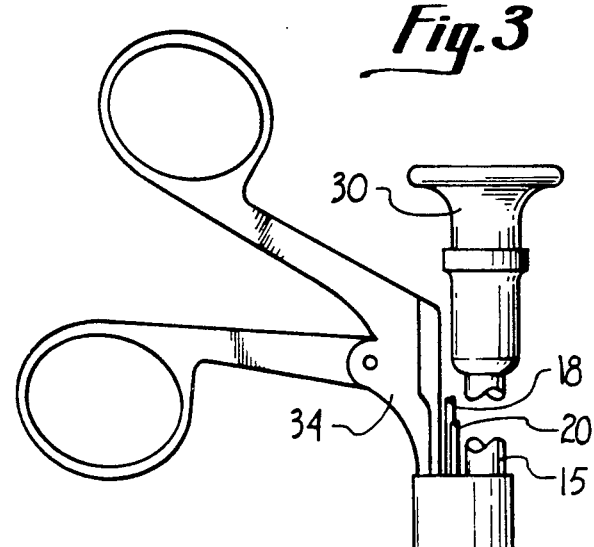
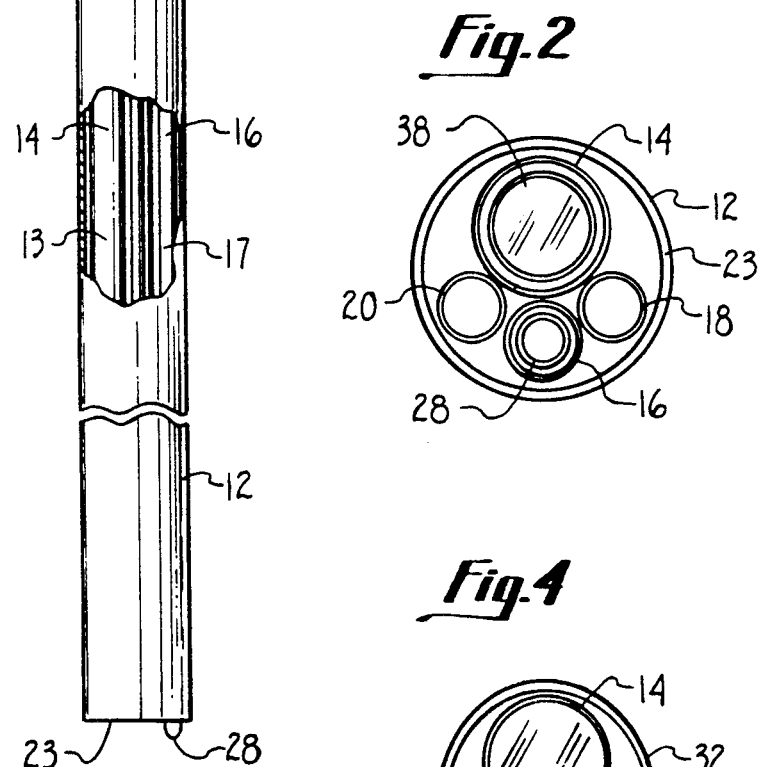
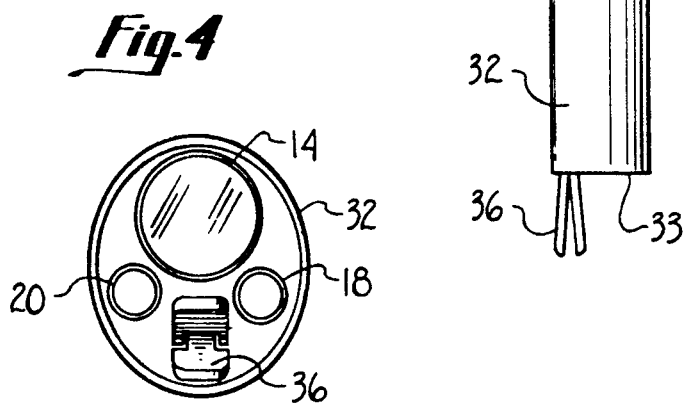

5,195,541

METHOD OF PERFORMING LAPAROSCOPIC LUMBAR DISCECTOMY

BACKGROUND OF THE INVENTION

Lumbar surgery to remove discs or portions of discs which have herniated has heretofore generally involved posterior entry. More recently, surgery using both endoscopic observation and control and a laser fiber instrument for incising the annulus and removing disc tissue has involved entry from one or two different posterior angles. Using such a technique, the endoscope is viewed from one angle, while the laser surgical tool or other surgical instrument is directed and guided during the surgery from a different angle. Such a procedure requires two spinal punctures into the patient thereby doubling the risk of nerve root injury. It is to the elimination of a dual puncture surgery for lumbar discectomy and to improve the control and observation of a lumbar discectomy utilizing a single disc entry that the present invention is directed. Although endoscopic surgical devices are known, such devices comprise elongated surgical forceps having a built-in tube for receiving an endoscope. However, such devices do not provide an endoscopic tool having a feature which allows insertion and removal of different selected surgical instruments during the surgery while the device itself remains in the abdominal cavity.

SUMMARY OF THE INVENTION

The present invention comprises a method and device for accomplishing a laparoscopic lumbar discectomy. The apparatus includes a single device inserted into the patient anteriorly and which device includes means for receiving an endoscope for observing and directing surgery, irrigation and suction means, and having surgical tool receiving means. In one embodiment, the apparatus of the invention includes a fitting for receiving and securing a fiber laser surgical device, together with endoscope receiving means and irrigation and suction tubes. In another embodiment, the invention comprises a device having endoscope receiving means, irrigation and suction tubes, and means for receiving a plurality of different conventional surgical instruments for carrying out one or more portions of a laparoscopic lumbar discectomy. In a third embodiment, the apparatus includes a 90° endoscopic elbow provided with means for mounting a video camera, and further optimally includes means for securing a light source. The invention also includes a method for performing the surgery utilizing the apparatus of the invention as will be explained hereinafter.

BRIEF DESCRIPTION OF THE DRAWINGS

FIG. 1 is a side view, partially broken away, illustrating the apparatus of the invention comprising an endoscope and fiber laser tool received therein;

FIG. 2 is an end view of the apparatus of FIG. 1;

FIG. 3 is a side view of another embodiment of the invention showing a device having a rongeur surgical instrument received therein;

FIG. 4 is an end view of the apparatus of FIG. 3;

DETAILED DESCRIPTION OF THE INVENTION

Figures 5, 6:
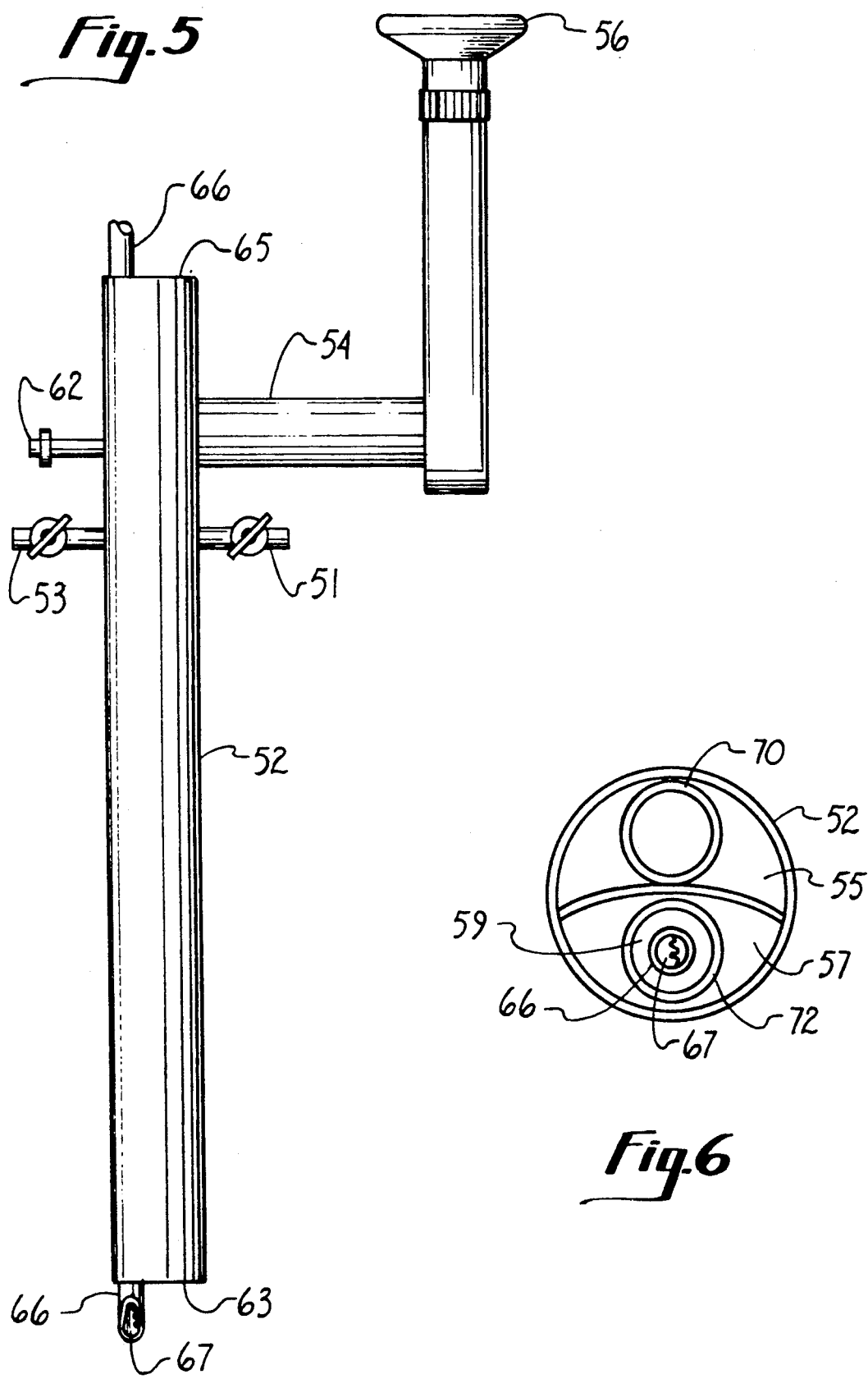
FIG. 5 is a side view of another embodiment having a 90° endoscopic elbow, and light source port and mounting components.
FIG. 6 is an end view of the device of FIG. 5.

Referring to FIGS. 1 and 2, there is illustrated a first embodiment of the apparatus of the invention having an endoscope and a fiber laser device received and secured therein. The specific components of the apparatus include a sleeve member 12 comprising an elongated cylinder having a first end 21 and a second end 23. The sleeve may be any desired shape, preferably round or oval, and having a relatively smooth exterior surface, without sharp edges or corners. The relative size of the sleeve is important. The length between the first and second ends must be sufficient to allow the surgeon or user to insert the device into a cavity of a patient, with the second end 23 adjacent the specific site of the surgery being carried out, and with the outer or first end 21 extending outwardly of the patient's cavity. For example, in abdominal or thoracic surgery, sleeve 12 must be a length of between about 15 and about 38 cm. However, it will be understood that different lengths for different specific uses may be used, and the criticality of the length will primarily be defined by the surgical procedure for which the device is to be used.

The cross-sectional outer diameter dimensions are also important, and must be large enough to accommodate the interior conduits, tubes, pipes, and other components, and yet be small enough to allow insertion into a relatively small incision, obviously preferable to minimize trauma. It has been found that a sleeve having a maximum exterior cross-sectional dimension of about 10 mm, and preferably between about 5 or about 9 mm is quite suitable for lumbar discectomy and many other procedures.

Interiorly of the sleeve 12 are secured an endoscope receiving means comprising a channel member 14 extending substantially entirely along the interior length of the sleeve between ends 21 and 23. Channel member 14 includes an interior portion 13, and an exterior portion 15 terminating in an adaptor or fitting 11 for receiving eyepiece 30 of an endoscope. The fitting may threadedly engage the endoscope for securing it in place, or it may simply otherwise allow the endoscope eyepiece to be nested in its proper position for use during surgery. In either event, the endoscope must be rotatable in the apparatus, to enable the user to rotate the endoscope to view the surgical site from any angle. The endoscope receiving channel or tube must also be of a shape to adequately receive and hold the elongated endoscope in place in the apparatus, as well as to provide positioning of the lens 38 substantially coterminous with the end 23 of sleeve 12. The channel also allows the user to conveniently grasp adaptor 11 and/or eyepiece 30 for rotating the endoscope eyepiece to observe the surgical site as well as to direct the apparatus through an incision and into the cavity where the surgery is performed.

A second channel member 16 is provided and secured in sleeve 12 for receiving and directing a laser fiber therealong. As shown, a laser fiber device having a handle member 25 and a laser emitter 28 at the opposite end is received and secured in channel member 16 having an interior portion 17 extending between ends 21 and 23 of sleeve 12 and an exterior portion 19 terminating in a fitting or adaptor 22 for securing the laser handle member 25. The laser fiber receiving means must be of sufficient length to allow the emitter 28 to be positioned properly adjacent sleeve end 23 when the fiber laser device is secured. It will be understood to those skilled in the art that different types of fiber lasers may be used and accommodated in the apparatus of the invention, including a free beam laser, such as $Co_2$, or a contact fiber laser, such as a Holmium or Nd:YAG type. Where a free beam laser is used, the fiber laser emitter 28 will usually extend beyond end 23 of sleeve 12 as illustrated in FIG. 1, while in the latter case, the fiber laser emitter may be coterminous with the sleeve end. Any suitable type of adaptor or fitting member 22 for securing the fiber laser surgical tool in the apparatus may be incorporated.

A plurality of conduits 18 and 20 to provide irrigation of the surgical site and to suction tissue and fluid to be removed from the site are provided by conduits 18 and 20. Any number of such irrigation and suction conduits may be installed in the device, depending on the type of surgery and needs of the surgeon and techniques or procedures in which the apparatus is to be used. The conduits may extend parallel adjacent the channel members as shown, or may be concentrically arranged as will be described hereinafter. The conduits preferably extend outwardly beyond first end 21 of sleeve 12, as shown, to provide means for being secured to hoses or pipes for directing irrigating fluid into the surgical site and removal of the fluid material therefrom. The length of the fluid handling conduits provides ports coterminous with a second end 23 of sleeve 12 and the conduits are secured and extend substantially along the interior length of the sleeve 12 as illustrated.

In FIGS. 3 and 4, there is illustrated another embodiment of the invention, also comprising a device having an endoscope securing feature as previously described, together with a plurality of fluid handling conduits for irrigating and suctioning the surgical site. In this embodiment, an alternative shape for sleeve 32 is illustrated, and is observed in FIG. 4 as being oval or oblong in cross-sectional shape. The device includes channel member 40 for receiving one or more of a plurality of different conventional surgical instruments. A conventional rongeur 34 is shown having blades 36 which may be actuated by the surgeon for cutting and removing bone or tissue. Although a rongeur is illustrated as being received in the device, it may be removed and other types of conventional surgical tools such as, for example, a free beam laser or a shaver, which may extend for some length beyond sleeve end 65 and substantially along the sleeve axis, and inserted, for example a trephine, curette, shaver or a trocar or other similar surgical tools, well known to those skilled in the art. Thus, any one of these surgical instruments may be conveniently inserted in the device and guided and manipulated by the surgeon having endoscopic observation for directing the apparatus through a patient's cavity to the surgical site and for manipulating and controlling the instrument. During the surgery, different surgical instruments may be selected by the surgeon and received in and removed from elongated channel 40 as the procedure dictates, with irrigation and suction being performed via fluid handling channels 18 and 20 and endoscopic observation and monitoring of the procedure provided using endoscope 30. Although both embodiments shown in FIGS. 1-4 illustrate the use of an eyepiece 30 on the endoscope, it will be understood that the endoscope will usually be attached to a video camera having projection means so that the surgeon may view and control the surgery by observing a conveniently located video screen.

Another embodiment of the apparatus of the invention is shown in FIGS. 5 and 6. In the embodiment shown, sleeve 52 is provided with an elbow 54 which extends out of the way of the plane and axis of the sleeve so that substantially straight cutting or surgical tools can be used without interfering with the observation of the surgery using an endoscope or attachment for a video camera. In such an embodiment, a 90° elbow 54 extends from the sleeve and is provided with an attachment device 56 for securing a video camera, or the like. Although the endoscopic 90° elbow is shown, a straight or angled attachment may be used for the same purpose, so long as it provides for endoscopic, video or other observation away from the axis of the sleeve to allow the surgeon to conveniently manipulate the tool extending from the sleeve. In addition, in the embodiment illustrated, fittings 51 and 53 for attaching irrigation and suction components are also provided, as is a light source attachment component 62. In this embodiment, a straight shaver apparatus 66 having a cutting end which can be extended outwardly up to a few centimeters from the end 63 of the sleeve is provided. Shaver 66 illustrated includes a port 67 and a hollow interior communicating with a suction port (not shown) for directing tissue suctioned from the surgical site through port 67, along the hollow shaver interior and out through a suction port attached to a power source handle, (not shown), and well understood by those skilled in the art.

Observing also FIG. 6, the sleeve of this embodiment may include one or more irrigation and/or suction conduits 55, 57 and 59 for introducing irrigating fluids and/or removing the tissue from the surgical site. If the device of the invention is to be used with a hollow shaver or other hollow surgical device through which tissue can be suctioned, a single port or multiple irrigation ports for directing irrigation fluid to the surgical site may be used. Where the surgical tool, for example a free beam laser, is to be used, both irrigation and suctioning the conduits are provided in the sleeve apparatus of the invention. As illustrated, the shape of such channels is not critical and, for example, one or more annular conduits 59 concentrically located around the surgical instrument may be incorporated, or other shaped channels may be conveniently formed along the sleeve interior adjacent the guide channels 70 and 72 for the endoscope and surgical tool.

Figure 7:
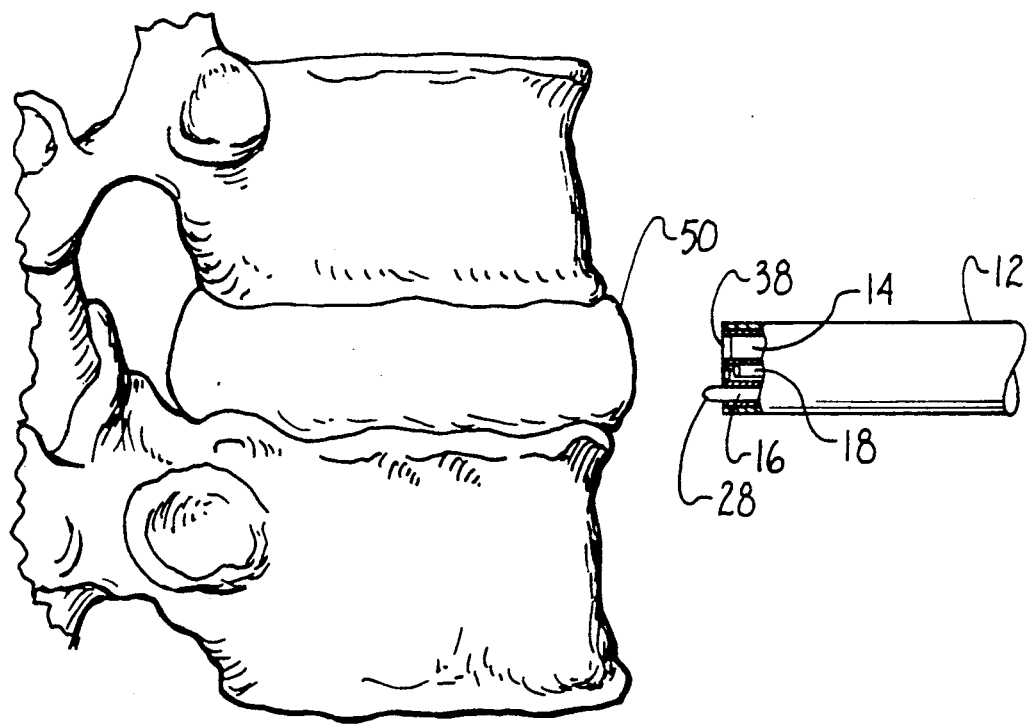
FIG. 7 illustrates a method of using the apparatus of FIG. 1 for laparoscopic lumbar discectomy.
Figure 8:
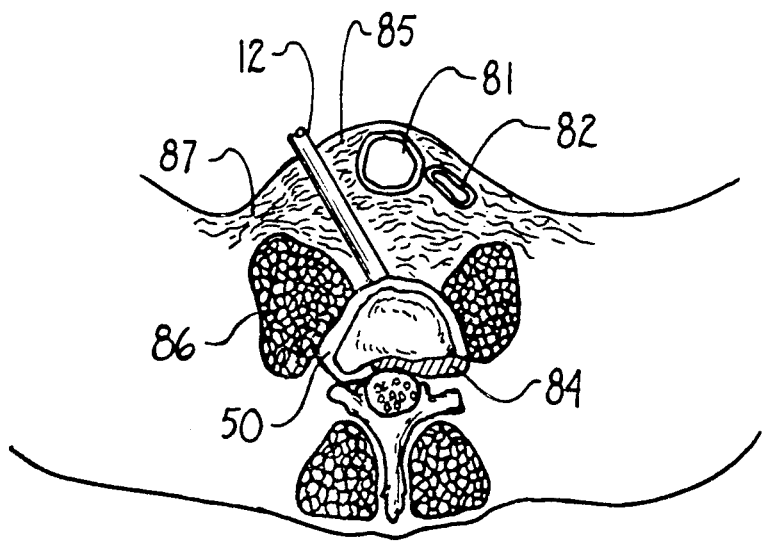
FIG. 8 further illustrates a method of performing surgery according to the invention.

FIGS. 7 and 8 schematically illustrates the use of the apparatus of FIG. 1 in a laparoscopic lumbar discectomy procedure of the invention which is believed to offer substantial advantages over state of the art lumbar discectomy procedures. In such a procedure, the patient is placed in a supine or lithotomy position, and the abdomen preferably distended with air or carbon dioxide. The surgeon observes the procedure preferably using a video camera attached to the endoscope and viewing the video screen. The surgeon directs the apparatus of the invention, including the cutting tool inserted in the appropriate channel of sleeve 12, through an abdominal incision, for example, immediately above the pubic bone. Direction is continued through soft tissue, which may be teased, coagulated or vaporized using the laser or other surgical tool until it is adjacent the exterior of the disc space annulus 50. Surgery carried out between lumbar vertebrae L3-4 and L4-5 may be accomplished by directing the sleeve 12 to the left of aorta 81 and inferior vena cava 82, between the aorta and the psoas muscle 86, and through the posterior peritoneum 87 and fatty tissue 85. If desired, the surgery may traverse through the psoas muscle. Where the surgery site is between L5 and S-1, the disection is preferably generally close to the midline between the iliac branches of the great vessels. Alternatively, for example, where the patent has extensive abdominal adhesions, it may be preferred to use a lateral puncture of the abdomen to avoid bowel perforation, and entry into the disc space is lateral, transversing the psoas muscle, or immediately in front of it. Once the apparatus reaches the exterior of the disc space annulus or ligament, a trephine may be used to penetrate the annulus and traverse the disc space, again using endoscopic and fluoroscopic control and guidance, and then proceed with the discectomy for removing herniated disc material 84. A fiber laser emitter 28 or other surgical device for cutting and removing bone and disc tissue is illustrated in FIG. 7. It is to be understood that the surgery or portion of the surgery may be conducted by utilizing any one or more different surgical instruments selected and alternately inserted and removed from sleeve 16. Concurrently with the cutting and removal of tissue, fluid is introduced into one or more of the channels for irrigating the surgical site, and suction is applied to one or more of the other conduits or through a shaver or other hollow cutting instrument for removing the fluid and tissue cut and loosened by the surgery. After the discectomy is complete, the surgeon removes the apparatus, applies appropriate sutures, and closes the wound incision in the abdomen. Conventional surgical techniques used as part of such a procedure are known to those skilled in the art. The improved laparoscopic lumbar discectomy of the invention avoids posterior dual puncture techniques used heretofore and may be accomplished in an outpatient setting with a minimum use of oral narcotics.

What is claimed is:

1. A method of performing laparoscopic lumbar discectomy comprising:
    securing a patient in a supine position with lumbar vertebrae at 12 o'clock relative to the aorta at 6 o'clock,
    inserting surgical apparatus comprising an elongated sleeve member having a first and a second end, endoscope receiving means and an endoscope secured therein, laser fiber receiving means having a laser fiber secured therein, and suction and irrigation channel means, each of said means extending along the interior of said sleeve member between said first and second ends through an abdominal incision at a location adjacent said 6 o'clock above the patient's lumbar vertebrae, directing said sleeve member from said incision through the abdominal cavity toward said lumbar vertebrae at 12 o'clock, observing the direction of said sleeve with said endoscope while guiding said sleeve member toward said 12 o'clock until the second end thereof is adjacent the exterior annulus of a lumbar disc space, surgically entering the disc space through said vertebra and removing disc tissue by energizing and manipulating said laser fiber, and directing irrigating fluid through one or more of said conduits and removing fluid with suctioning through one or more of said conduits.

2. A method of claim 1, including directing said sleeve member from said incision toward said lumbar vertebrae through a space between the aorta and the psoas muscle.

3. A method of performing laparoscopic lumber discectomy comprising:
    securing a patient in a supine position with lumbar vertebrae at 12 o'clock relative to the aorta at 6 o'clock,
    providing an apparatus comprising an elongated, substantially axial sleeve member having a first end and a second opposite end, one or more conduits along the interior length of said sleeve member between said first and second ends thereof for directing fluids therethrough, each of said conduits having a portion extending exteriorally from said sleeve member and a first port adjacent the end thereof for communicating with suction or irrigation means and having a second port adjacent an opposite end thereof substantially coterminous with the second end of said sleeve member, and a first elongated hollow tube for receiving an endoscope and an endoscope secured therein, and a second elongated hollow tube for removably receiving different selected elongated surgical instruments including a laser fiber, rongeur, trephine, curette, shaver and trocar, said first and second tubes secured in and extending along the interior length of said sleeve member between said first and second ends,
    securing a selected one of said surgical instruments along said second hollow tube, inserting said apparatus through an abdominal incision at a location adjacent said 6 o'clock and above the patient's lumbar vertebrae, and directing said sleeve member downwardly from said incision through the abdominal cavity toward said lumbar vertebrae at 12 o'clock until the second end thereof is adjacent the exterior annulus of a disc space while observing the direction of said sleeve with said endoscope, manipulating said selected surgical instrument for engaging disc tissue, and directing irrigating fluid into one or more of said conduits and suctioning said fluid through other of said one or more conduits.

4. A method of claim 3, including directing said apparatus through said abdominal cavity from said incision toward said lumbar vertebrae between the aorta and left psoas muscle, through the annulus and into the disc space.

* * * * *